United States Patent
Zhao et al.

(10) Patent No.: US 10,179,110 B2
(45) Date of Patent: Jan. 15, 2019

(54) DISPERSION COMPRISING A PARTIALLY NEUTRALIZED ESTERIFIED CELLULOSE ETHER

(71) Applicant: Dow Global Technologies LLC, Midland, MI (US)

(72) Inventors: Jin Zhao, Midland, MI (US); Roland Adden, Bomlitz (DE); Neal J. Fetner, Midland, MI (US); David L. Malotky, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/308,792

(22) PCT Filed: Apr. 28, 2015

(86) PCT No.: PCT/US2015/027863
§ 371 (c)(1),
(2) Date: Nov. 3, 2016

(87) PCT Pub. No.: WO2015/179072
PCT Pub. Date: Nov. 26, 2015

(65) Prior Publication Data
US 2017/0181977 A1    Jun. 29, 2017

Related U.S. Application Data

(60) Provisional application No. 62/000,709, filed on May 20, 2014.

(51) Int. Cl.
*A61K 9/48* (2006.01)
*B29C 41/14* (2006.01)

(52) U.S. Cl.
CPC ............ *A61K 9/4816* (2013.01); *B29C 41/14* (2013.01)

(58) Field of Classification Search
None
See application file for complete search history.

(56) References Cited

U.S. PATENT DOCUMENTS

| 4,226,981 A | 10/1980 | Onda et al. |
| 4,365,060 A | 12/1982 | Onda et al. |
| 5,539,021 A | 7/1996 | Pate et al. |
| 5,910,319 A | 6/1999 | Anderson et al. |
| 2009/0297565 A1 | 12/2009 | Müller |
| 2012/0016364 A1 | 1/2012 | Mayse et al. |
| 2013/0295188 A1* | 11/2013 | Cade ............. A61K 9/4816 424/494 |

FOREIGN PATENT DOCUMENTS

| EP | 0648487 A1 | 4/1995 |
| EP | 0662323 A1 | 7/1995 |
| EP | 0677322 A2 | 10/1995 |
| EP | 2476439 A1 | 7/2012 |
| GB | 2325623 A | 12/1998 |
| GB | 2353215 A | 2/2001 |
| JP | 55053215 A | 4/1980 |
| JP | 8109124 A | 4/1996 |
| WO | 8000659 A1 | 4/1980 |
| WO | 9610995 A1 | 4/1996 |
| WO | 2013164121 A1 | 11/2013 |
| WO | 2013164122 A1 | 11/2013 |

OTHER PUBLICATIONS

Particle Sciences, "Nanotechnology: New Name, Old Science", Technical Brief 2011, pp. 1-2.*

* cited by examiner

*Primary Examiner* — Brian Gulledge
(74) *Attorney, Agent, or Firm* — Ballard Spahr LLP

(57) ABSTRACT

An aqueous composition comprising at least 10 weight percent of a dispersed esterified cellulose ether, based on the total weight of the aqueous composition, wherein the esterified cellulose ether comprises (i) groups of the formula —C(O)—R—COOH or (ii) a combination of aliphatic monovalent acyl groups and groups of the formula —C(O)—R—COOH, R being a divalent aliphatic or aromatic hydrocarbon group, and at least a part of the groups —C(O)—R—COOH are neutralized with an ammonium salt of carbonic acid, formic acid or acetic acid, and wherein d90 of the dispersed esterified cellulose ether particles is up to 10 micrometers, d90 being the diameter where 90 mass percent of the particles have a smaller equivalent diameter and the other 10 mass percent have a larger equivalent diameter, is useful for preparing coating dosage forms including tablets, capsules and others, or for the formation of capsules shells.

13 Claims, No Drawings

DISPERSION COMPRISING A PARTIALLY NEUTRALIZED ESTERIFIED CELLULOSE ETHER

FIELD

This invention concerns aqueous compositions comprising dispersed at least partially neutralized esterified cellulose ethers, processes for producing the compositions, and coated dosage forms and capsule shells made from the aqueous compositions.

INTRODUCTION

Esters of cellulose ethers, their uses and processes for preparing them are generally known in the art. Known methods of producing cellulose ether-esters include the reaction of a cellulose ether with an aliphatic monocarboxylic acid anhydride or a dicarboxylic acid anhydride or a combination thereof, for example as described in U.S. Pat. Nos. 4,226,981 and 4,365,060.

Various known esterified cellulose ethers are useful as enteric polymers for pharmaceutical dosage forms, such as methylcellulose phthalate (MCP), hydroxypropyl methylcellulose phthalate (HPMCP), methylcellulose succinate (MCS), or hydroxypropyl methylcellulose acetate succinate (HPMCAS). The esterified cellulose ethers are used for coating dosage forms, such as tablets, microparticulates or capsules. Enteric polymers protect the drug from inactivation or degradation in the acidic environment or prevent irritation of the stomach by the drug, but are dissolved in the intestinal canals to release the drug contained therein. U.S. Pat. No. 4,365,060 discloses enterosoluble capsules which are said to have excellent enterosolubility behavior.

Enteric coatings or capsules can be prepared from organic or aqueous solutions of esterified cellulose ethers. European Patent Applications EP 0 662 323 and EP 0 677 322 disclose methods of preparing an aqueous emulsion for coating solid pharmaceutical preparations wherein a cellulosic polymer is dissolved in an organic solvent miscible with water or in a mixture of the organic solvent with water to give a polymer solution having a polymer concentration of not more than 10 wt. %, the solution is mixed with (additional) water to disperse the solution in water, and then organic solvent is removed. The published Japanese Patent Application JP8109124-A discloses the production of coating powders from such emulsions by adding an anionic surfactant and spray-drying. However, organic solvents are often not desirable for pharmaceutical or nutritional uses. Hence, organic solutions of esterified cellulose ethers are sought to be replaced by aqueous solutions.

The UK Patent Application GB 2 353 215 discloses the use of a buffering agent with high vapor pressure, such as ammonium hydrogen carbonate, to increase the pH of water to 7.8 and to dissolve enteric polymers, such as cellulose acetate phthalate (CAP), hydroxypropyl methylcellulose phthalate (HPMCP), hydroxypropyl methylcellulose acetate succinate (HPMCAS) or polymethacrylic acid esters. Upon drying of the aqueous coating solution, the buffer evaporates and changes the polymer to its non-ionized from. U.S. Patent application 2009/0297565 discloses the use of aqueous solutions of enteric polymers neutralized with ammonium bicarbonate for coating very fine drug particles. Unfortunately, only very dilute solutions can be achieved by this method. The neutralized aqueous solutions only comprise 4-6 percent of the enteric polymer, based on the amount of water. Such solutions require much time and energy for drying.

In view of the known disadvantages of organic and aqueous solutions of esterified cellulose ethers, the skilled artisans have spent much research effort on aqueous dispersions of enteric polymers.

European Patent Application EP 0 648 487 discloses an aqueous dispersion comprising 5 to 15 wt. % of an enteric coating base, such as HPMCAS or HPMCP. The aqueous dispersion further comprises 15-40 wt. % of a plasticizer, such as triethyl citrate or triacetin, and 0.1-10 wt. % of an anionic surfactant, such as sodium alkyl sulfate, or a sodium or potassium salt of a fatty acid, based on the weight of HPMCAS or HPMCP. However, the necessity to use such a large amount of plasticizer is a significant disadvantage.

International Patent Publication WO 96/10995 discloses an enteric film coating dry powder composition for use in making an aqueous enteric coating suspension which comprises an enteric film forming polymer, preferably a polyvinyl acetate phthalate, a detackifier, a viscosity modifier, and an alkalizing agent. The enteric polymer has a particle size such that 90% of the polymer particles are under 25 microns, preferably under 13 microns. The alkalizing agent acts as an anti-coalescing agent or stabilizing agent and reduces the tackiness of the coating. The viscosity modifier assists in film forming, acts as a suspending agent for the insoluble components in the composition and adds viscosity to the coating suspension. However, aqueous enteric coating suspensions wherein the enteric polymer has particles sizes of up to 13 micrometers or even up to 25 micrometers are not able to form stable suspensions or dispersions in the absence of a substantial amount of adjuvants which may jeopardize the enteric properties of the final film.

U.S. Pat. No. 5,910,319 discloses an enteric fluoxetine pellet comprising a) a core layer consisting of fluoxetine and an excipient, b) an optional separating layer, c) an enteric layer comprising HPMCAS, and d) an optional finishing layer. The US Patent discusses that when the enteric polymer is applied as an aqueous suspension, a problem in obtaining a uniform, coherent film often results. It is important that the suspension remains homogeneous and that conditions which favor the agglomeration of the polymer do not occur. Cooling the HPMCAS suspension below 20° C. before application and cooling the tubing and nozzle that are used to apply the HPMCAS suspension to a substrate is advisable. Due to the complexities experienced with HPMCAS suspensions, U.S. Pat. No. 5,910,319 suggests that it is preferred to apply the enteric coating as aqueous solution whenever it is possible. In the case of HPMCAS, full or partial neutralization by adding ammonia, preferably in the form of aqueous ammonium hydroxide is recommended. In a specific embodiment an enteric coating suspension comprising 6 wt. % HPMCAS was fully neutralized by adding 0.47 wt. ammonium hydroxide. Unfortunately, such amount of HPMCAS in an aqueous suspension is unduly low.

US Patent Application Publication US 2012/0161364 discloses an aqueous composition for an enteric hard capsule comprising an enteric base material, such as HPMCAS or HPMCP, a capsule forming aid, such as a cellulose ether, and a neutralizing agent, such as sodium hydroxide, aqueous ammonia, potassium hydroxide, or calcium hydroxide. The amount of the enteric base material is said to be 8-25 percent, based on the total weight of the aqueous composition. According to the working examples the amount HPMCP is 14-20 wt.-%, whereas the amount of HPMCAS is about 15 wt.-%. Unfortunately, capsules prepared from such compositions all require extensive neutralization, leaving a high amount of neutralizing agent in the capsules, which jeopardizes the enteric properties of the capsules.

International Patent Application WO 2013/164122 discloses an aqueous composition for the manufacture of capsule shells comprising 5-50 wt. % of a wide range of functional polymers. In the majority of the examples the capsules are produced from an Aquacoat CPD 30 dispersion, which is a 30 wt. % aqueous dispersion comprising 23 wt. % non-salified cellulose acetate phthalate (CAP) and 7 wt. % Poloxamer, optionally blended with a minor amount of a HPMCAS slurry. Often uniform films can be obtained. A HPMCAS dispersion comprising 14% solids is also disclosed. Although 20% triethyl citrate is used as a film forming aid, when pins are heated to 50° C. and dipped into the dispersion, the HPMCAS polymer aggregates but the film rapidly collapses and flows down.

International Patent Application WO 2013/164121 discloses an aqueous composition comprising HPMCAS polymer dispersed in water, wherein the polymer is partially neutralized with at least one alkaline material, such as ammonia, sodium hydroxide, calcium hydroxide, potassium hydroxide, cationic polymers, and mixtures thereof. The amount of polymer is said to range from 15-25 percent, based on the total weight of the aqueous composition. The Examples of WO 2013/164121 illustrate the preparation of HPMCAS films prepared from aqueous dispersions comprising 16-20 wt. % solids.

Although a higher content of HPMCAS solids in the aqueous dispersion is possible and improved films can be prepared when using a partially neutralized HPMCAS as disclosed in WO 2013/164121 than when using a non-salified HPMCAS as disclosed in WO 2013/164122, there is still the urgent need to provide aqueous dispersions of HPMCAS or other esterified cellulose ethers which have improved film-forming properties. Also there is still the need to provide aqueous dispersions that comprise a reasonably high concentration of HPMCAS or other esterified cellulose ethers. A reasonably high concentration of HPMCAS or other esterified cellulose ethers in the aqueous dispersion reduces the costs of transporting the dispersion prior its use and decreases the time and energy required to remove water when preparing films from the dispersion. Surprisingly, it has been found that the new aqueous dispersions as described below have improved film-forming properties.

SUMMARY

One aspect of the present invention is an aqueous composition which comprises at least 10 weight percent of a dispersed esterified cellulose ether, based on the total weight of the aqueous composition, wherein the esterified cellulose ether comprises
(i) groups of the formula —C(O)—R—COOH or
(ii) a combination of aliphatic monovalent acyl groups and groups of the formula —C(O)—R—COOH,
R being a divalent aliphatic or aromatic hydrocarbon group, and
at least a part of the groups —C(O)—R—COOH are neutralized with an ammonium salt of carbonic acid, formic acid or acetic acid, and
wherein d90 of the dispersed esterified cellulose ether particles is up to 10 micrometers, d90 being the diameter where 90 mass percent of the particles have a smaller equivalent diameter and the other 10 mass percent have a larger equivalent diameter.

Another aspect of the present invention is a process for producing the above-mentioned aqueous composition, wherein the process comprises the steps of
grinding, in the presence of an aqueous diluent, an esterified cellulose ether comprising (i) groups of the formula —C(O)—R—COOH or (ii) a combination of aliphatic monovalent acyl groups and groups of the formula —C(O)—R—COOH, wherein R is a divalent aliphatic or aromatic hydrocarbon group, and
blending an ammonium salt of carbonic acid, formic acid or acetic acid and optionally one or more adjuvants with the esterified cellulose ether before, during or after the grinding of the esterified cellulose ether to neutralize at least a part of the groups —C(O)—R—COOH,
wherein aqueous diluent, esterified cellulose ether, ammonium salt of carbonic acid, formic acid or acetic acid and the optional adjuvant(s) are added in such amounts that the weight of the esterified cellulose ether is at least 10 weight percent, based on the total weight of the aqueous composition.

Yet another aspect of the present invention is a process for producing the above-mentioned aqueous composition, wherein the process comprises the steps of
melting a) an esterified cellulose ether comprising (i) groups of the formula
—C(O)—R—COOH or (ii) a combination of aliphatic monovalent acyl groups and groups of the formula —C(O)—R—COOH, wherein R is a divalent aliphatic or aromatic hydrocarbon group,
emulsifying the molten esterified cellulose ether in b) an aqueous diluent,
adding c) an ammonium salt of carbonic acid, formic acid or acetic acid, and optionally d) one or more adjuvants before, during or after the step of emulsifying the molten esterified cellulose ether in the aqueous diluent to neutralize at least a part of the groups —C(O)—R—COOH,
wherein the components a), b), c) and optionally d) are added in such amounts that the weight of the esterified cellulose ether is at least 10 weight percent, based on the total weight of the aqueous composition, and
cooling the emulsion to form an aqueous dispersion.

Yet another aspect of the present invention is a dosage form which is coated with a coating prepared from the above-mentioned aqueous composition.

Yet another aspect of the present invention is a capsule shell which is made from the above-mentioned aqueous composition.

Yet another aspect of the present invention is a capsule which comprises an above-mentioned capsule shell and further comprises a drug or a nutritional or food supplement or a combination thereof.

Yet another aspect of the present invention is a process for producing a capsule shell which comprises the steps of providing the above-mentioned aqueous composition, pre-heating molding pins to a temperature higher than the aqueous composition, dipping the pre-heated molding pins into the aqueous composition, forming a film on said molding pins by withdrawing said pins from said aqueous composition, and drying the film on the molding pins.

DESCRIPTION OF EMBODIMENTS

Surprisingly, it has been found that films, such as capsules or coatings, of good quality and high transparency can be prepared from the new aqueous compositions as described below. The aqueous composition comprises the dispersed esterified cellulose ether at reasonably high concentration.

Thus evaporation of unduly high amounts of aqueous diluent can be avoided when preparing films, such as capsules or coatings.

The esterified cellulose ether comprised in the composition of the present invention has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether comprised in the composition of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as an esterified hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylating agent, e.g. a methylating agent, and/or a hydroxyalkylating agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxyl units are covalently bound to each other by ether bonding. Within this definition it is not important whether the terminal hydroxyl group of a hydroxyalkoxyl substituent is further alkylated or not; both alkylated and non-alkylated hydroxyalkoxyl substituents are included for the determination of MS(hydroxyalkoxyl). The esterified cellulose ether generally has a molar substitution of hydroxyalkoxyl groups of at least 0.05, preferably at least 0.08, more preferably at least 0.12, and most preferably at least 0.15. The degree of molar substitution is generally not more than 1.00, preferably not more than 0.90, more preferably not more than 0.70, and most preferably not more than 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers preferably have a DS(alkoxyl) of at least 1.0, more preferably at least 1.1, even more preferably at least 1.2, most preferably at least 1.4, and particularly at least 1.6. The DS(alkoxyl) is preferably not more than 2.5, more preferably not more than 2.4, even more preferably not more than 2.2, and most not more than 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether utilized in the present invention has (i) groups of the formula —C(O)—R—COOH or (ii) a combination of aliphatic monovalent acyl groups and groups of the formula —C(O)—R—COOH, wherein R is a divalent aliphatic or aromatic hydrocarbon group and a part of the groups —C(O)—R—COOH are neutralized with an ammonium salt of carbonic acid, formic acid or acetic acid.

The aliphatic monovalent acyl groups are preferably selected from the group consisting of acetyl, propionyl, and butyryl, such as n-butyryl or i-butyryl.

Preferred groups of the formula —C(O)—R—COOH are —C(O)—CH$_2$—CH$_2$—COOH, —C(O)—CH=CH—COOH or —C(O)—C$_6$H$_4$—COOH. In the groups of formula —C(O)—C$_6$H$_4$—COOH the carbonyl group and the carboxylic group are preferably arranged in ortho-positions.

Preferred esterified cellulose ethers are i) HPMCXY, wherein HPMC is hydroxypropyl methyl cellulose, X is A (acetate), or X is B (butyrate) or X is Pr (propionate) and Y is S (succinate), or Y is P (phthalate) or Y is M (maleate), such as hydroxypropyl methyl cellulose acetate phthalate (HPMCAP), hydroxypropyl methyl cellulose acetate maleate (HPMCAM), or hydroxypropyl methylcellulose acetate succinate (HPMCAS), or ii) hydroxypropyl methyl cellulose phthalate (HPMCP), hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); and methyl cellulose acetate succinate (MCAS).

Hydroxypropyl methylcellulose acetate succinate (HPMCAS) is the most preferred esterified cellulose ether.

The esterified cellulose ethers generally have a degree of substitution of aliphatic monovalent acyl groups, such as acetyl, propionyl, or butyryl groups, of not more than 1.75, preferably not more than 1.50, more preferably not more than 1.25, and most preferably not more than 1.00, or even not more than 0.65. The degree of substitution of aliphatic monovalent acyl groups can be zero, but preferably it is at least 0.05, more preferably at least 0.10, and most preferably at least 0.20.

The esterified cellulose ethers comprised in the coatings, capsules and capsule shells generally have a degree of substitution of partially neutralized groups of formula —C(O)—R—COOH, such as partially neutralized succinoyl, of at least 0.05, preferably at least 0.10. The degree of substitution of partially neutralized groups of formula —C(O)—R—COOH generally is up to 1.6, preferably up to 1.30, more preferably up to 1.00, and most preferably up to 0.70 or even up to 0.60.

The sum of i) the degree of substitution of aliphatic monovalent acyl groups and ii) the degree of substitution of partially neutralized groups of formula —C(O)—R—COOH is generally at least 0.05, preferably at least 0.10, more preferably at least 0.20, most preferably at least 0.30, and particularly at least 0.40. The mentioned sum is generally no more than 2.0, preferably no more than 1.4, more preferably no more than 1.15, most preferably no more than 1.10 and particularly no more than 1.00.

The term "partially neutralized groups of formula —C(O)—R—COOH" as used herein means that a part of the groups —C(O)—R—COOH are neutralized with an ammonium salt of carbonic acid, formic acid or acetic acid. Preferred ammonium salts of carbonic acid, formic acid or acetic acid are ammonium carbonate, ammonium hydrogen carbonate, ammonium formate, or ammonium acetate. Ammonium hydrogen carbonate is most preferred. Most preferably, the esterified cellulose ether is hydroxypropyl methyl cellulose acetate succinate that is partially neutralized with ammonium carbonate or ammonium hydrogen carbonate.

The content of the acetate and succinate ester groups is determined according to "Hypromellose Acetate Succinate", United States Pharmacopeia and National Formulary, NF 29, pp. 1548-1550. Irrespective of whether the succinate ester groups are present in the esterified cellulose ether in their acidic or neutralized form, the content of succinate ester groups is determined as succinoyl groups in their acidic form (—CO—CH$_2$—CH$_2$—COOH).

Reported values are corrected for volatiles (determined as described in section "loss on drying" in the above HPMCAS monograph). The method may be used in analogue manner to determine the content of propionyl, butyryl, phthalyl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) - \left(\% \text{ HPO} * \frac{M(OCH_2CH(OH)CH_3) - M(OH)}{M(OCH_2CH(OH)CH_3)}\right) - \left(\% \text{ Acetyl} * \frac{M(COCH_3) - M(H)}{M(COCH_3)}\right) - \left(\% \text{ Succinoyl} * \frac{M(COC_2H_4COOH) - M(H)}{M(COC_2H_4COOH)}\right)$$

$$DS(\text{Me}) = \frac{\frac{\% \text{ MeO}}{M(OCH_3)}}{\frac{\% \text{ cellulose backbone}}{M(AGU)}} \quad MS(\text{HP}) = \frac{\frac{\% \text{ HPO}}{M(HPO)}}{\frac{\% \text{ cellulose backbone}}{M(AGU)}}$$

$$DS(\text{Acetyl}) = \frac{\frac{\% \text{ Acetyl}}{M(\text{Acetyl})}}{\frac{\% \text{ cellulose backbone}}{M(AGU)}}$$

$$DS(\text{Succinoyl}) = \frac{\frac{\% \text{ Succinoyl}}{M(\text{Succinoyl})}}{\frac{\% \text{ cellulose backbone}}{M(AGU)}}$$

$M(\text{MeO}) = M(OCH_3) = 31.03$ Da $M(\text{Acetyl}) = M(COCH_3) = 43.04$ Da $M(AGU) = 162.14$ Da  $M(OH) = 17.0008$ Da  $M(H) = 1.008$ Da $M(\text{HPO}) = M(OCH_2CH(OH)CH_3) = 75.09$ Da $M(\text{Succinoyl}) = M(COC_2H_4COOH) = 101.08$ Da By convention, the weight percent is an average weight percentage based on the total weight of the cellulose repeat unit, including all substituents. The content of the methoxyl group is reported based on the mass of the methoxyl group (i.e., —OCH$_3$). The content of the hydroxyalkoxyl group is reported based on the mass of the hydroxyalkoxyl group (i.e., —O— alkylene-OH); such as hydroxypropoxyl (i.e., —O—CH$_2$CH(CH$_3$)—OH). The content of the aliphatic monovalent acyl groups is reported based on the mass of —C(O)—R$_1$ wherein R$_1$ is a monovalent aliphatic group, such as acetyl (—C(O)—CH$_3$). The content of the group of formula —C(O)—R—COOH is reported based on the mass of this group, such as the mass of succinoyl groups (i.e., —C(O)—CH$_2$—CH$_2$—COOH).

The esterified cellulose ether comprised in the composition, coating, capsule shells or capsules of the present invention generally has a viscosity of at least 1.2 mPa·s, preferably least 1.8 mPa·s, and more preferably least 2.4 mPa·s, and generally no more than 200 mPa·s, preferably no more than 100 mPa·s, more preferably no more than 50 mPa·s, and most preferably no more than 30 mPa·s, measured as a 2.0 weight percent solution of the esterified cellulose ether in 0.43 weight-% aqueous NaOH at 20° C. according to "Hypromellose Acetate Succinate, United States Pharmacopia and National Formulary, NF 29, pp. 1548-1550".

The aqueous composition of the present invention comprises at least 10 percent, preferably at least 15 percent, and more preferably at least 20 percent, and under some conditions even at least 25 percent of esterified cellulose ether(s) in dispersed state in the aqueous composition, based on the total weight or the aqueous composition. The aqueous composition of the present invention generally comprises up to 40 percent or up to 35 percent of the esterified cellulose ether(s) in dispersed state in the aqueous composition, based on the total weight or the aqueous composition. The aqueous composition of the present invention can comprise one, two or more types of the above-described esterified cellulose ethers, but their total amount should be in the ranges indicated above.

In the aqueous composition of the present invention at least a part of the groups —C(O)—R—COOH in the esterified cellulose ether(s) are neutralized with an ammonium salt of carbonic acid, formic acid or acetic acid. Preferably only a part of the groups —C(O)—R—COOH are neutralized. More preferably the groups —C(O)—R—COOH are neutralized to such extent that the esterified cellulose ether is dispersed but not dissolved in the aqueous composition.

This allows a high concentration of the esterified cellulose ether in the aqueous composition while maintaining a sufficiently low viscosity such that the aqueous composition can still be conveniently handled. In the aqueous composition of the present invention preferably at least 5 mol percent, more preferably at least 10 mol percent, most preferably at least 15 mol percent or 20 percent, and particularly at least 30 or 40 mol percent of the groups of formula —C(O)—R—COOH in the esterified cellulose ethers are neutralized with an ammonium salt of carbonic acid, formic acid or acetic acid. Preferably up to 80 mol percent, more preferably up to 70 mol percent, most preferably up to 60 mol percent, and particularly up to 50 mol percent of the groups of formula —C(O)—R—COOH are neutralized with an ammonium salt of carbonic acid, formic acid or acetic acid. Preferred ammonium salts of carbonic acid, formic acid or acetic acid are ammonium carbonate, ammonium hydrogen carbonate, ammonium formate, or ammonium acetate. Ammonium hydrogen carbonate is most preferred. Preferably, ammonium salt of carbonic acid, formic acid or acetic acid is incorporated in such amount into the aqueous composition that the resultant pH of the composition is at least 4.0, more preferably at least 4.3, and most preferably at least 4.6; and preferably up to 6.0, more preferably up to 5.5, and most preferably up to 5.2, measured at 23° C. To achieve such degree of neutralization, typically at least 0.02 mmols, preferably at least 0.05 mmols, and more preferably at least 0.10 mmols, and typically up to 0.60 mmols, preferably up to 0.40 mmols, and more preferably up to 0.30 mmols of ammonium salt of carbonic acid, formic acid or acetic acid are incorporated into the aqueous composition per mmole of groups of formula —C(O)—R—COOH that are comprised in the aqueous composition. The skilled artisan knows how much ammonium salt of carbonic acid, formic acid or acetic acid is suitably blended with the esterified cellulose ether, based on the molecular weight of the ammonium salt of carbonic acid, formic acid or acetic acid, the molecular weight of the anhydroglucose unit of the esterified cellulose ether, the degree of substitution of the groups of formula —C(O)—R—COOH, and the mole percent of the groups —C(O)—R—COOH in the esterified cellulose ethers that is desired to be neutralized with an ammonium salt of carbonic acid, formic acid or acetic acid. For example, when hydroxypropyl methyl cellulose acetate succinate is partially neutralized with ammonium hydrogen carbonate, preferably at least 0.3 g, more preferably at least 1.0 g, and most preferably at least 1.5 g of ammonium hydrogen carbonate or ammonium carbonate is used per 100 g of hydroxypropyl methyl cellulose acetate succinate. Preferably up to 5.0 g, more preferably up to 2.5 g, and most preferably up to 1.9 g of ammonium hydrogen carbonate or ammonium carbonate is used per 100 g of hydroxypropyl methyl cellulose acetate succinate.

Surprisingly, it has been found that films, such as capsules or coatings, of better quality, such as an increased transparency, can be produced from the aqueous dispersion if a part of the groups —C(O)—R—COOH are neutralized with the ammonium salt of carbonic acid, formic acid or acetic acid, such as ammonium hydrogen carbonate, than if a part of the groups —C(O)—R—COOH are neutralized with other alkaline materials, such as sodium hydroxide.

The aqueous composition of the present invention is in the form of an aqueous dispersion, typically in the form of a stable dispersion. The dispersed esterified cellulose ether has a d90 of up to 10 micrometers, typically up to 8 micrometers, more typically up to 6 micrometers, most typically even only up to 5 and in many cases even only up to 4 micrometers or even only up to 3 micrometers, d90 being the diameter where 90 mass percent of the particles have a smaller equivalent diameter and the other 10 mass percent have a larger equivalent diameter. The equivalent particle diameter d is the diameter of a sphere having the same volume as the volume of a given particle. The dispersed esterified cellulose ether typically has a d90 of 0.7 micrometers or more, more typically 1.0 micrometers or more, and most typically 1.5 micrometers or more.

The mean particle diameter is typically 0.5 micrometers or more, more typically 0.7 micrometers or more, and most typically 0.8 micrometers or more; and typically up to 8 micrometers, more typically up to 6 micrometers, even more typically up to 4 micrometers, and most typically even only up to 3 micrometers or even only up to 2 micrometers.

The median particle size, d50, of the dispersed esterified cellulose ether particles is generally up to 7 micrometers, typically up to 5 micrometers, more typically up to 3 micrometers, most typically even only up to 2 micrometers, and in many cases even only up to 1.5 micrometers. The median particle size, d50, of the dispersed esterified cellulose ether particles is typically 0.3 micrometers or more, more typically 0.5 micrometers or more, and most typically 0.7 micrometers or more. The median particle size d50 is the diameter where 50 mass percent of the particles have a smaller equivalent diameter and 50 mass percent have a larger equivalent diameter.

The particle sizes are measured by laser diffraction particle size analysis, e.g., using a Beckman Coulter laser diffraction particle size analyzer which is commercially available from Beckman Coulter, Calif.

The aqueous composition of the present invention comprises an aqueous diluent. The aqueous diluent is water, optionally mixed with a minor amount of an organic solvent. The aqueous diluent preferably consists of 50 to 100 weight percent, more preferably 65 to 100 weight percent, and most preferably 75 to 100 weight percent of water and preferably 0 to 50 weight percent, more preferably 0 to 35 weight percent, and most preferably 0 to 25 weight percent of an organic solvent, based on the total weight of water and the organic solvent. Useful organic solvents are polar organic solvents having one or more heteroatoms, such as oxygen, nitrogen or halogen like chlorine. More preferred organic solvents are alcohols, preferably monofunctional alcohols, such as methanol, ethanol, isopropanol or n-propanol; ethers, such as tetrahydrofuran, ketones, such as acetone; methyl ethyl ketone, or methyl isobutyl ketone; acetates, such as ethyl acetate; halogenated hydrocarbons, such as methylene chloride; or nitriles, such as acetonitrile. Preferably the aqueous composition of the present invention comprises water alone as aqueous diluent. The amount of the aqueous diluent is typically at least 50 percent, more typically at least 60 percent, and most typically at least 65 percent, based on the total weight of the aqueous composition. The amount of the aqueous diluent is typically no more than 85 percent, more typically no more than 80 percent, and most typically no more than 75 percent, based on the total weight of the aqueous composition.

In one embodiment the at least partially neutralized esterified cellulose ether(s) described above amounts to at least 50 percent, typically at least 60 percent, and more typically at least 80 percent; and up to 100 percent, typically up to 99 percent, more typically up to 95 percent, and most typically up to 90 percent of the total amount of the ingredients of the aqueous composition excluding the aqueous diluent. For example, in one embodiment the aqueous composition comprises the dispersed esterified cellulose ether and one or more polymers different from an esterified cellulose ether, provided that the dispersed esterified cellulose ether is at least 50 percent, preferably at least 60 percent, and more preferably at least 80 percent; and up to 99 percent, typically up to 95 percent, and more typically up to 90 of the total weight of the polymers in the aqueous composition.

The aqueous composition of the present invention may further comprise optional ingredients, for example active ingredients, such as fertilizers, herbicides or pesticides, or biologically active ingredients, such as vitamins, herbals and mineral supplements and drugs; or adjuvants such as one or more dispersants, plasticizers, gelling agents, film forming aids, coloring agents, pigments, opacifiers, flavor and taste improvers, antioxidants, and any combination thereof. Optional additives are preferably pharmaceutically acceptable. The amount of these optional ingredients is typically from 0 to 50 percent of the total weight of the ingredients of the aqueous composition excluding the aqueous diluent. Typically the amount is 1 percent or more, more typically 5 percent or more, and most typically 10 percent or more; and up to 40 percent, more typically up to 20 percent, and most typically up to 10 percent of the total weight of the ingredients of the aqueous composition excluding the aqueous diluent.

In one embodiment, the aqueous composition of the present invention further comprises at least one film forming aid. The term "film forming aid" comprises one or more plasticizers conventionally used in the manufacture of coatings or capsule shells, notably hard capsule shells, to ensure the formation of self-supported cohesive films and avoid capsule brittleness, and/or one or more viscosity enhancers at elevated temperature, i.e. natural as well as synthetic substances conventionally used to optimize aqueous compositions for coating purposes or the dip molding manufacture of hard capsule shells.

Film forming aids that display plasticizing properties include: phthalic esters, such as dimethyl-, diethyl-, and diisopropyl-phthalate; citric esters, such as triethyl-, tributyl-, acetyltriethyl- and acetyltributyl-citrate; phosphoric esters, such as triethyl-, tricresyl, and triphenyl-phosphate; alkyl lactate; glycol esters; glycerol and glyceryl esters, such as glycerol triacetate also known as triacetine; sucrose esters; oils and fatty acid esters; butyl stearate; dibutyl sebacate; dibutyl tartrate; diisobutyl adipate, tributyrin; propylene glycol; and mixtures thereof. It has surprisingly been found that in the composition of the present invention, wherein the esterified cellulose ether comprises at least partially neutralized groups of formula —C(O)—R—COOH, the amount of plasticizer can be reduced or the usage of a plasticizer can even be avoided while still obtaining films of acceptable quality, such as capsules or coatings. In comparable compositions wherein the groups of formula —C(O)—R—COOH in the esterified cellulose ether have not been neutralized, the film quality is lower and/or a higher amount of plasticizer has to be used, which is often not desirable for food or pharmaceutical uses.

In one embodiment, film forming aids are cellulose ethers, such as carboxy methylcellulose, hydroxypropyl cellulose, ethyl cellulose, methylcellulose, hydroxypropylmethylcellulose (HPMC), e.g. HPMC types 2910, 2906 and/or 2208 as defined in USP30-NF25; gelatin, pullulan, non enteric starch derivatives, such as hydroxypropyl starch; polyvinyl acetate derivatives (PVAP); sorbitan monoesters; sorbitan polyoxyethylene esters; fatty acid esters; glycerol polyethylene, glycol ricinoleate; macrogolglycerides; triethyl citrate (TEC); acetyl trialkyl citrate; glycerol triacetate (triacetine); talc; and mixtures thereof.

In one embodiment, one or more film forming aids are present in the aqueous composition in an amount ranging from 0 to 20% by weight, such as 0 to about 15% by weight, or 0 to 10% by weight, based on the total weight of the aqueous composition of the present invention.

In one embodiment one or more dispersants are present in the aqueous composition in an amount ranging from 0 to 20 percent, based on the weight of the dispersed esterified cellulose ether. A typical amount of one or more dispersants is at least 0.1 percent, preferably at least 0.3 percent, more preferably at least 0.5 percent, most preferably at least 0.8 percent, and particularly at least 1.0 percent, based on the total weight of the esterified cellulose ether(s). The total amount of dispersant is preferably up to 15 percent, more preferably up to 12 percent, even more preferably up to 10 percent or 8 percent, and most preferably up to 6.0 percent, or even only up to 5.0 percent, based on the total weight of the esterified cellulose ether(s). Well-known anionic surfactants are sodium alkyl sulfates, such as sodium dodecyl sulfate. Well-known non-ionic surfactants are ethylene oxide-propylene oxide block copolymers, such as Pluronic™ surfactants, or polyoxyethylene sorbitan monooleates, such as Polysorbate 80, also known under the trademark Tween 80. However, if a surfactant is used, preferably a salt of a fatty acid is utilized. Preferred fatty acid salts are ammonium, alkali metal or alkaline earth metal salts. Preferred alkali metal ions are the sodium or potassium ions. A preferred alkaline earth metal ion is the calcium ion. The fatty acids can be saturated or unsaturated. Exemplary of saturated fatty acids are caprylic acid, capric acid, lauric acid, myristic acid, palmitic acid, stearic acid, arachidic acid, behenic acid, lignoceric acid and cerotic acid. The unsaturated fatty acids can be mono-, di- or triunsaturated fatty acids, mono-unsaturated and di-unsaturated fatty acids being preferred. Exemplary of mono-unsaturated fatty acids are myristoleic acid, palmitoleic acid, sapienic acid, oleic acid, elaidic acid and vaccenic acid. Exemplary of di-unsaturated fatty acids are linoleic acid and linoelaidic acid. Ammonium, alkali metal and alkaline earth metal salts of stearic acid or oleic acid are most preferred, particularly those salts mentioned above.

The aqueous composition of the present invention can be prepared by various methods. One method includes grinding the esterified cellulose ether in the presence of an aqueous diluent and optionally in the presence of one or more adjuvants. Another method includes melting or softening the esterified cellulose ether at an elevated temperature, optionally in the presence of one or more adjuvants, and emulsifying the molten or softened mass in the aqueous diluent. Preparing an aqueous composition by simply physically blending an esterified cellulose ether, an ammonium salt of carbonic acid, formic acid or acetic acid, and an aqueous diluent at room temperature is usually not suitable for preparing a stable dispersion.

In one embodiment the process for producing the aqueous composition of the present invention comprises the steps of grinding, in the presence of an above-described aqueous diluent, at least one esterified cellulose ether as described above, and blending an ammonium salt of carbonic acid, formic acid or acetic acid and optionally one or more adjuvants with the esterified cellulose ether before, during or after the grinding of the esterified cellulose ether to neutralize at least a part of the groups of formula —C(O)—R—COOH. The aqueous diluent, esterified cellulose ether, ammonium salt of carbonic acid, formic acid or acetic acid and the optional adjuvant(s) are added in such amounts that the weight of the esterified cellulose ether is at least 10 weight percent, based on the total weight of the aqueous composition. Preferred amounts are those indicated further above. Any grinding device suitable for grinding esterified cellulose ethers in the presence of an aqueous diluent to a particle size d90 as indicated further above can be used. Preferred grinding devices are wet grinding units such as media mills or bead mills. The grinding is typically conducted at a temperature of at least 2° C., more typically at least 15° C., and typically at a temperature of up to 40° C., more typically up to 35° C. Grinding is conducted for a sufficient time period to achieve an above-mentioned particle size d90 of the dispersed esterified cellulose ether particles.

In another embodiment the process for producing the aqueous composition of the present invention comprises the steps of melting a) an esterified cellulose ether as described above and emulsifying the molten esterified cellulose ether in b) an above-described aqueous diluent, adding c) an ammonium salt of carbonic acid, formic acid or acetic acid, and optionally d) one or more adjuvants before, during or after the step of emulsifying the molten esterified cellulose ether in the aqueous diluent to neutralize at least a part of the groups —C(O)—R—COOH, wherein the components a), b), c) and optionally d) are added in such amounts that the weight of the esterified cellulose ether is at least 10 weight percent, based on the total weight of the aqueous composition, and cooling the emulsion to form an aqueous dispersion. Preferred amounts are those indicated further above. This embodiment of the process is preferably conducted in an extruder. Alternatively, a pressurized batch kneader can be used for conducting this embodiment of the invention.

In a preferred embodiment the process for producing the aqueous composition of the present invention comprises the steps of melting the esterified cellulose ether and optionally one or more adjuvants in a melt zone of an extruder to form a melt, conveying the melt to an emulsification zone of the extruder in which the temperature and pressure are controlled; feeding aqueous diluent, an ammonium salt of carbonic acid, formic acid or acetic acid, and optionally one or more adjuvants into the emulsification zone, wherein the melt is emulsified in the added components, conveying the produced emulsion to a dilution and cooling zone of the extruder; and feeding aqueous diluent, optionally one or more salts of a fatty acid, and optionally one or more adjuvants into the dilution and cooling zone to dilute the emulsion thereby forming an aqueous dispersion. The general process conditions and equipment which may be used to perform the process are disclosed in U.S. Pat. No. 5,539,021, the disclosure of which is incorporated herein by reference.

Alternatively, a pressurized batch kneader can be used for conducting the steps of melting an above-described esterified cellulose ether, emulsifying the molten esterified cellulose ether in an aqueous diluent, adding an ammonium salt of carbonic acid, formic acid or acetic acid and optionally one or more adjuvants before, during or after the step of emulsifying the molten esterified cellulose ether in the aqueous diluent, and cooling the emulsion to form an aqueous dispersion.

In the melt-extrusion processes described above the melting step is preferably conducted at a temperature of from 100 to 155° C., more preferably from 125 to 145° C., and at a pressure from 5 to 35 bar, more preferably from 15 to 25 bar. The emulsification step is preferably conducted at a temperature of from 100 to 155° C., more preferably from 115 to 135° C., and at a pressure from 4 to 35 bar, more preferably from 15 to 25 bar. The cooling step is preferably conducted at a temperature of from 45 to 100° C., more preferably from 70 to 90° C., and at a pressure from 1 to 35 bar, more preferably from 1 to 5 bar.

Suitable and preferred types and amounts of esterified cellulose ethers, ammonium salts of carbonic acid, formic acid or acetic acid, optional adjuvants and aqueous diluents in the processes for producing the aqueous composition of the present invention are described further above. The ammonium salt(s) of carbonic acid, formic acid or acetic acid and optional adjuvants are preferably added before or during the grinding of the esterified cellulose ether or the step of emulsifying the molten esterified cellulose ether in the aqueous diluent. The ammonium salt(s) of carbonic acid, formic acid or acetic acid and optional adjuvants can also be added after the grinding of the esterified cellulose ether or after the step of emulsifying the molten esterified cellulose ether, but preferably at least 50 percent of the ammonium salt(s) of carbonic acid, formic acid or acetic acid that is used for preparing the aqueous composition of the present invention is added before or during the grinding or emulsification of the esterified cellulose ether.

In one aspect of the invention the aqueous composition of the present invention may be used for coating dosage forms, such as tablets, granules, pellets, caplets, lozenges, suppositories, pessaries or implantable dosage forms, to form a coated composition. If the aqueous composition of the present invention comprises an active ingredient, such as a drug, drug layering can be achieved, i.e., the dosage form and the coating may comprise different active ingredients for different end-uses and/or having different release kinetics. The coating can be carried out in a known manner, for example by known dipping or spraying processes. The process for coating dosage forms comprises the step of drying the produced coating on the dosage form.

In yet another aspect of the invention the aqueous composition of the present invention may be used for the manufacture of capsules shells in a process which comprises the step of contacting the aqueous composition with dipping pins. According to one embodiment the process for producing capsule shells comprises the steps of providing the aqueous composition of the present invention as described above, pre-heating molding pins to a temperature higher than the aqueous composition, dipping the pre-heated molding pins into the aqueous composition, forming a film on said molding pins by withdrawing said pins from said aqueous composition, and drying the film on the molding pins. Preferably hard capsule shells are produced. The general process conditions and equipment which may be used to prepare capsules shells are described in International Patent Application Nos. WO 2013/164122 and WO 2013/164121, the disclosures of which are incorporated herein by reference. The capsule shells can take the form of caps and bodies, which are then removed from the pins. Caps are mated with bodies to form capsules.

Without wanting to be bound to the theory, Applicant believes that residual by-product of the neutralization reaction, such as $H_2CO_3$, acts as plasticizer via associating with the succinic groups —C(O)—R—COOH when the aqueous composition is contacted with preheated molding pins that have a temperature higher than the aqueous composition and when the aqueous composition forms a film on the molding pins during the dipping process.

The above-mentioned processes for coating dosage forms or for producing capsules comprise a drying step. Typical drying temperatures are 55° C. or more, preferably 65° C. or more, and more preferably 75° C. or more. Typical drying temperatures are up to 90° C., preferably up to 85° C., and more preferably up to 80° C. When the produced film is dried, such as a coating on a dosage form or a capsule shell on the molding pins, residual ammonium salt(s) of carbonic acid, formic acid or acetic acid typically decompose at the drying temperature. For example, ammonium hydrogen carbonate ($NH_4HCO_3$) decomposes to $NH_3$, $CO_2$ and $H_2O$ at about 60° C. or more at atmospheric pressure. Without wanting to be bound to the theory, Applicant believes that the evaporation of $NH_3$ and $CO_2$ in addition to $H_2O$ contributes to setting of the film on the molding pins or of the coating on a substrate resulting in a homogeneous film. The dried coatings or capsule shells and capsules do not comprise substantial amounts of residual alkaline material. This is a great advantage as compared to the capsules disclosed in WO 2013/164121. The capsules disclosed in WO 2013/164121 comprise alkaline material that does not evaporate upon drying.

Moreover, during drying of the films, e.g. the coatings on a substrate or the capsule shells on the molding pins, at elevated temperature some or nearly all of the neutralized groups —C(O)—R—COO$^-$NH$_4^+$ in the esterified cellulose ether are transformed back into their acidic form:

—C(O)—R—COO$^-$NH$_4^+$ ↔ —C(O)—R—COOH+ NH$_3$(↑).

Esterified cellulose ethers that comprise acidic groups —C(O)—R—COOH have enteric properties, i.e., they are substantially insoluble in gastric fluid and rapidly dissolve in intestinal fluid. Accordingly, the aqueous composition of the present invention is particularly useful for coating dosage forms including tablets, capsules and others, or for the formation of capsules shells, all preferably for enteric use, i.e., coatings or capsules shells that are dissolved in the intestinal canals to release the active ingredient like a drug contained in the dosage form or in the capsules. Hard capsule shells are preferred.

In the coatings, capsule shells and capsules prepared from the aqueous composition of the present invention, particularly in the dried coatings, capsule shells and capsules, typically 3 mol percent or more, more typically 5 mol percent or more, and most typically 10 mol percent or more, but typically not more than 50 mol percent, more typically not more than 30 mol percent, and most typically not more than 20 mol percent of the groups of formula —C(O)—R—COOH in the esterified cellulose ether(s) are still neutralized with an ammonium salt of carbonic acid, formic acid or acetic acid. Another aspect of the invention are capsules, particularly hard capsules, that comprise a capsule shell of the invention and that further comprise one or more drugs and/or one or more nutritional or food supplements, such as one or more vitamins, herbals or mineral supplements. The drug, nutritional or food supplement is surrounded by the shell material of the present invention. The hard capsules are preferably two-piece hard capsules. The capsule shells in the form of caps and bodies can be prepared as described above. One or more drugs and/or one or more nutritional or food supplements can be placed into capsules bodies, caps can be mated with bodies to form capsules and the formed capsules can be sealed according to methods known in the art.

Some embodiments of the invention will now be described in detail in the following Examples.

EXAMPLES

Unless otherwise mentioned, all parts and percentages are by weight. In the Examples the following test procedures are used.

Viscosity of Hydroxypropyl Methyl Cellulose Acetate Succinate (HPMCAS)

A 2.0% by weight solution of the HPMCAS in 0.43 wt. % aqueous NaOH was prepared as described in "Hypromellose Acetate Succinate, United States Pharmacopia and National Formulary, NF 29, pp. 1548-1550, followed by an Ubbelohde viscosity measurement at 20° C. according to DIN 51562-1:1999-01 (January 1999).

Acid Dissociation Constant (pKa) of HPMCAS

The pKa of HPMCAS was measured with the following titration method. About 0.4 g of a HPMCAS sample was accurately weighed into a 200 mL polyethylene titration beaker and diluted with about 60 mL of ultra-pure water purified by a Milli-Q process. The solution was then stirred on a magnetic stir plate using a Teflon stir bar and 0.1M NaOH was added until the solution pH was increased to pH 7-8. The temperature of the solution was kept at 23° C. After dissolution, the sample was titrated on a Metrohm 904 Titrando using 0.1M HCl with continuous stirring. A titration curve was generated and pKa was determined by determining the pH value at half of the volume at equivalent point.

$$pH - \log\left(\frac{[-CO\text{-}CH2\text{-}CH2\text{-}COO^-]}{[-CO\text{-}CH2\text{-}CH2\text{-}COOH]}\right) = pKa$$

Content of Ether and Ester Groups of HPMCAS

The content of ether groups in HPMCAS was determined in the same manner as described for "Hypromellose", United States Pharmacopeia and National Formulary, USP 35, pp 3467-3469.

The ester substitution with acetyl groups (—CO—CH$_3$) and the ester substitution with succinoyl groups (—CO—CH$_2$—CH$_2$—COOH) and neutralized succinoyl groups were determined according to Hypromellose Acetate Succinate, United States Pharmacopia and National Formulary, NF 29, pp. 1548-1550". Reported values for ester substitution were corrected for volatiles (determined as described in section "loss on drying" in the above HPMCAS monograph). The DS$_{succinoyl}$ is determined as succinoyl groups in their acidic form (—CO—CH$_2$—CH$_2$—COOH).

DS(succinoyl)=DS(—CO—CH2-CH2-COO$^-$)+DS(—CO—CH2-CH2-COOH)

HPMCAS Particle Size Measurement in the Aqueous Dispersion

To measure particle sizes 1-2 g of the aqueous HPMCAS dispersion that had been produced as described below was diluted in 20 ml of purified water. The particle size in the diluted dispersion was measured by laser diffraction particle size analysis using a Beckman Coulter LS 13 320 laser diffraction particle size analyzer which is commercially available from Beckman Coulter, Calif. The Universal Liquid Module (ULM) with a Fraunhofer optical model, a Polarization Intensity Differential Scattering (PIDS) system and a sonication control unit were used. In the sonication control unit the HPMCAS dispersion was subjected to ultrasonic treatment for a time period of up to 120 seconds during the HPMCAS addition (about 30 seconds) and particle size measurement (about 90 seconds).

Determination of Solids Content in the Aqueous Dispersion

The solids content was determined using a moisture balance (Mettler Toledo Advanced Moisture Analyzer, Model HB43-S). Instrument settings were as follows: 3 g dispersion using the Rapid drying program with a temperature set point of 120° C. (40% overshoot for first 3 minutes) with switch-off criteria 5 (less than 1 mg weight change over 140 seconds). Upon drying to remove water, the residual solids content (including all additives) was weighed.

Degree of Neutralization of the Succinoyl Groups in the Aqueous Dispersion

The percentage of neutralized succinoyl groups, based on the total number of succinoyl groups, in the aqueous dispersion was calculated from the pH value of the dispersion, measured at 23° C., and the pKa of the HPMCAS according to the following formula:

$$100 \times \frac{10^{(pH-pKa)}}{1 + 10^{(pH-pKa)}} = \text{percentage of neutralized succinoyl groups.}$$

Degree of Neutralization of the Succinoyl Groups in the Dried Film

The mol percentage of neutralized succinoyl groups, based on the total number of succinoyl groups, in the dried film can be detected as the residual moles of $NH_4^+$, which is equivalent to residual moles of N in the dried film. The elemental analysis of N in the dried film was performed on a Flash 2000 Organic Elemental Analyzer (Thermo Fisher Scientific).

$$\frac{N \text{ detected in weight \%} * \text{molecular weight of } AGU \text{ in } \frac{g}{mol}}{DS(\text{succinoyl}) * 14 \text{ g/mol}} =$$

mol percentage of neutralized succinoyl groups

HPMCAS Used for Preparing the Aqueous Dispersion in Example 1 and Comparative Example A HPMCAS was used that had
23.2% methoxyl groups ($DS_{methoxyl}$=1.9),
7.3% hydroxypropoxyl groups ($MS_{hydroxypropoxyl}$=0.25),
9.3% acetyl groups ($DS_{acetyl}$=0.55),
11.2% succinoyl groups ($DS_{succinoyl}$=0.28),
a molecular weight of AGU (anhydroglucose unit) of 255 g/mol,
a pKa of 5.1, and
and a viscosity of 2.91 mPa·s, measured as a 2.0% by weight solution of the HPMCAS in 0.43 wt. % aqueous NaOH.

To evaluate the film-forming properties of an esterified cellulose ether, such as HPMCAS, of which a part of the groups —C(O)—R—COOH are neutralized with an ammonium salt of carbonic acid, formic acid or acetic acid, such as ammonium hydrogen carbonate, instead of being partially neutralized with another alkaline material, such as sodium hydroxide, dispersions were prepared that consisted only of the partially neutralized HPMCAS and water and that comprised no adjuvants such as film-forming aids. Films were prepared from these dispersions.

Comparative Example A (not Prior Art)

To produce an aqueous HPMCAS dispersion, water was loaded first and recirculated through a Netzsch LAB STAR media mill (1.4 mm Ytterum Stabilized Zirconia media, 0.7 mm screen size). During the milling process HPMCAS solids were loaded gradually to water having a temperature of 15-25° C. and recirculating through the mill at a mill speed of 3600 rev/min. Addition of HPMCAS was continued until a total solids loading of about 20% was achieved, based on the total amount of the composition. At this point, 10 wt. % NaOH solution was added to adjust the pH to 5.1. Final addition of HPMCAS was loaded into mill to adjust the final solid concentration. Milling continued until the final median particle size, d50, of 0.77 m was obtained. The total amount of NaOH in the final dispersion was about 0.26 wt. %.

The resultant degree of neutralization of succinoyl groups was 48 mol percent, i.e., 48 mol percent of the groups —CO—$CH_2$—$CH_2$—COOH of the HPMCAS comprised in the aqueous dispersion were neutralized and present as —CO—$CH_2$—$CH_2$—$COO^-Na^+$ groups. The resultant dispersion had a solids content of 20.3 weight percent and a pH of 5.1. The HPMCAS particles had a median particle size, d50, of 0.77 micrometers, a mean particle size of 1.0 micrometer and a particle size d90 of 2.0 micrometers.

The dispersion was cast on a T-fal AirBake non-stick cookie sheet. The dispersion was poured evenly across the top of the cookie sheet just below the 50 mil (1.27 mm) portion of the draw down bar. The bar was drawn smoothly across the cookie sheet over a period of 3-5 seconds. The cookie sheet with dispersion on top was then put in the oven that set at 56° C. for 2 hrs. The cookie sheet was covered with another cookie sheet and a dish of water inside to slow the evaporation. Upon evaporation of the water a milky free-standing film was obtained.

The resultant degree of neutralization of succinoyl groups was still 48 mol percent, i.e., 48 mol percent of the groups —CO—$CH_2$—$CH_2$—COOH in the HPMCAS comprised in the dried film were neutralized and present as —CO—$CH_2$—$CH_2$—$COO^-Na^+$ groups. This high amount of —CO—$CH_2$—$CH_2$—$COO^-Na^+$ groups jeopardizes the acid and water resistance of the film.

Example 1

To produce an aqueous HPMCAS dispersion, water was loaded first and recirculated through a Netzsch LAB STAR media mill (1.4 mm Ytterum Stabilized Zirconia media, 0.7 mm screen size). During the milling process HPMCAS solids were loaded gradually to water having a temperature of 15-22° C. and recirculating through the mill at a mill speed of 3600 rev/min. Addition of HPMCAS was continued until a total solids loading of about 20% was achieved, based on the total amount of the composition. At this point, $NH_4HCO_3$ solid was added to the mill followed by 10 wt. % $NH_4HCO_3$ solution to adjust the pH to 4.9. Milling continued until the final median particle size, d50, of 0.94 m was obtained. The total amount of $NH_4HCO_3$ in the final dispersion was about 0.31 wt. %.

The resultant degree of neutralization of succinoyl groups was 41 mol percent, i.e., 41 mol percent of the groups —CO—$CH_2$—$CH_2$—COOH of the HPMCAS comprised in the aqueous dispersion were neutralized and present as —CO—$CH_2$—$CH_2$—$COO^-NH_4^+$ groups. The resultant dispersion had a solids content of 19.7 weight percent and a pH of 4.9. The HPMCAS particles had a median particle size, d50, of 0.94 micrometers, a mean particle size of 1.1 micrometer and a particle size d90 of 2.1 micrometers.

The dispersion was cast on a T-fal AirBake non-stick cookie sheet and subsequently dried as described in Comparative Example A. Upon evaporation of the water a free-standing, relatively clear film was obtained.

The resultant residual degree of neutralization of succinoyl groups was less than about 1.4 mol percent, i.e., less than about 1.4 mol percent of the groups —CO—$CH_2$—$CH_2$—COOH in the HPMCAS comprised in the dried film were neutralized and present as —CO—CH$_2$—CH$_2$—COO$^-$NH$_4^+$ groups. Hence, the film produced from the aqueous dispersion of the present invention has an excellent acid and water resistance.

The dispersion of Example 1 formed a film that was more transparent and less milky than the film produced according to Comparative Example A. The films produced according to Comparative Example A and Example 1 were visually evaluated by 23 people. The people were not informed about the chemical composition and did not know which film represented the invention and which film was the comparative film. All 23 people designated the same film as more clear and less milky than the other one. The film that was designated as more clear and less milky was the film of Example 1, i.e., the film produced from the aqueous dispersion of the present invention. The less clear and more milky film was the one prepared from the comparative aqueous dispersion of Comparative Example A.

The invention claimed is:

1. An aqueous composition comprising at least 10 weight percent of a dispersed hydroxypropyl methyl cellulose acetate succinate, based on the total weight of the aqueous composition, wherein in the aqueous composition at least a part of the succinate groups of the hydroxypropyl methyl cellulose acetate has been neutralizing with ammonium carbonate or ammonium hydrogen carbonate, and
    wherein d90 of the dispersed hydroxypropyl methyl cellulose acetate succinate particles is up to 10 micrometers, d90 being the diameter where 90 mass percent of the particles have a smaller equivalent diameter and the other 10 mass percent have a larger equivalent diameter.

2. The aqueous composition of claim 1 wherein the median particle size d50 of the dispersed hydroxypropyl methyl cellulose acetate succinate particles is up to 5 micrometers, d50 being the diameter where 50 mass percent of the particles have a smaller equivalent diameter and 50 mass percent have a larger equivalent diameter.

3. The aqueous composition of claim 1 comprising at least 15 weight percent of the dispersed hydroxypropyl methyl cellulose acetate succinate, based on the total weight of the aqueous composition.

4. The aqueous composition of claim 1 wherein in the aqueous composition the hydroxypropyl methyl cellulose acetate succinate has been partially neutralized with ammonium carbonate or ammonium hydrogen carbonate.

5. The aqueous composition of claim 1 comprising the dispersed hydroxypropyl methyl cellulose acetate succinate and one or more polymers different from an esterified cellulose ether, provided that the dispersed hydroxypropyl methyl cellulose acetate succinate is at least 50 percent of the total weight of the polymers in the aqueous composition.

6. The aqueous composition of claim 1 additionally comprising at least one adjuvant selected from the group consisting of dispersants, plasticizers, gelling agents, film forming aids, coloring agents, pigments, opacifiers, flavor and taste improvers, and antioxidants.

7. The aqueous composition of claim 1 comprising at least 10 weight percent of dispersed hydroxypropyl methyl cellulose acetate succinate that is partially neutralized with ammonium carbonate or ammonium hydrogen carbonate, based on the total weight of the aqueous composition, d90 of the dispersed hydroxypropyl methyl cellulose acetate succinate particles being up to 5 micrometers and d50 of the dispersed hydroxypropyl methyl cellulose acetate succinate particles is up to 3 micrometers.

8. A process for producing the aqueous composition of claim 1 comprising the steps of grinding, in the presence of an aqueous diluent, a hydroxypropyl methyl cellulose acetate succinate and
    blending ammonium carbonate or ammonium hydrogen carbonate and optionally one or more adjuvants with the hydroxypropyl methyl cellulose acetate succinate before, during or after the grinding of the hydroxypropyl methyl cellulose acetate succinate to neutralize at least a part of the succinate groups,
    wherein aqueous diluent, hydroxypropyl methyl cellulose acetate succinate, ammonium carbonate or ammonium hydrogen carbonate, and the optional adjuvant(s) are added in such amounts that the weight of the hydroxypropyl methyl cellulose acetate succinate is at least 10 weight percent, based on the total weight of the aqueous composition.

9. A process for producing the aqueous composition of claim 1 comprising the steps of
    melting a) a hydroxypropyl methyl cellulose acetate succinate,
    emulsifying the molten hydroxypropyl methyl cellulose acetate succinate in b) an aqueous diluent,
    adding c) ammonium carbonate or ammonium hydrogen carbonate, and optionally d) one or more adjuvants before, during or after the step of emulsifying the molten hydroxypropyl methyl cellulose acetate succinate in the aqueous diluent to neutralize at least a part of the succinate groups,
    wherein the components a), b), c) and optionally d) are added in such amounts that the weight of the hydroxypropyl methyl cellulose acetate succinate is at least 10 weight percent, based on the total weight of the aqueous composition, and
    cooling the emulsion to form an aqueous dispersion.

10. A dosage form being coated with a coating prepared from the aqueous composition of claim 1.

11. A capsule shell made from the aqueous composition of claim 1.

12. A capsule comprising a capsule shell of claim 11 and further comprising a drug or a nutritional or food supplement or a combination thereof.

13. A process for producing a capsule shell comprising the steps of
    providing the aqueous composition of claim 1,
    pre-heating molding pins to a temperature higher than the aqueous composition,
    dipping the pre-heated molding pins into the aqueous composition,
    forming a film on said molding pins by withdrawing said pins from said aqueous composition, and
    drying the film on the molding pins.

* * * * *